US008622934B2

(12) United States Patent
Muzslay et al.

(10) Patent No.: US 8,622,934 B2
(45) Date of Patent: Jan. 7, 2014

(54) GUIDEWIRE WITH TWO FLEXIBLE END PORTIONS AND METHOD OF ACCESSING A BRANCH VESSEL THEREWITH

(75) Inventors: Heath Muzslay, Kalamazoo, MI (US); Emilie Johnson, Cotati, CA (US); Matthew Haggard, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 301 days.

(21) Appl. No.: 13/093,631

(22) Filed: Apr. 25, 2011

(65) Prior Publication Data

US 2012/0271397 A1 Oct. 25, 2012

(51) Int. Cl.
*A61B 5/00* (2006.01)
*A61B 19/00* (2006.01)
*A61M 25/00* (2006.01)
*A61F 2/06* (2013.01)

(52) U.S. Cl.
USPC ........... 600/585; 600/434; 623/1.13; 128/898

(58) Field of Classification Search
USPC ................ 606/194, 195, 198; 623/1.11, 1.12, 623/1.13, 1.23, 1.35
See application file for complete search history.

(56) References Cited

U.S. PATENT DOCUMENTS

| | | | |
|---|---|---|---|
| 4,545,390 A | 10/1985 | Leary | |
| 5,421,349 A | 6/1995 | Rodriguez et al. | |
| 5,492,530 A | 2/1996 | Fischell et al. | |
| 5,713,917 A | 2/1998 | Leonhardt | |
| 5,824,040 A * | 10/1998 | Cox et al. | 623/1.35 |
| 5,824,041 A | 10/1998 | Lenker et al. | |
| 6,139,540 A * | 10/2000 | Rost et al. | 600/585 |
| RE37,148 E | 4/2001 | Shank | |
| 6,641,606 B2 * | 11/2003 | Ouriel et al. | 623/1.12 |
| 7,264,632 B2 | 9/2007 | Wright et al. | |
| 7,621,880 B2 * | 11/2009 | Ryan et al. | 600/585 |
| 2007/0244413 A1 | 10/2007 | Biggins | |
| 2010/0305475 A1 | 12/2010 | Hinchliffe et al. | |

FOREIGN PATENT DOCUMENTS

WO   WO 2008/100877 A2   8/2008

OTHER PUBLICATIONS

Greenberg et al. "Endovascular Repair of Thoracoabdominal Aneurysms"; 2008.
Ferreira et al. "Branched Devices for Thoracoabdominal Aneurysm Repair: early Experience", 2008.
Schroeder, Jurgen, "The Mechanical Properties of Guidewires. Part I: Stiffness and Torsional Strength", CardioVascular and Interventional Radiology, Springer-Verlag New York, Inc. 1993.
Kadir, Saadoon, "A Multipurpose, Double-Ended Guide Wire" AJR 143:626, Sep. 1984.

* cited by examiner

*Primary Examiner* — Tuan V Nguyen (57) ABSTRACT

A guidewire having flexible or floppy proximal and distal end portions is used for percutaneously accessing a branch vessel through a deployed prosthesis having at least one fenestration near an ostium of the branch vessel. The prosthesis is delivered and deployed via a first percutaneous access site. The guidewire extends over the outside surface of the deployed prosthesis and extends through the at least one fenestration. The flexible distal end portion is snared via a second percutaneous access site and is pulled in a direction towards the second percutaneous access site until the flexible proximal end of the guidewire is located adjacent to the branch vessel. A guide catheter is then advanced over the guidewire until it cannulates the branch vessel. The flexible proximal end of the guidewire may then be advanced into the branch vessel and used for delivery of a branch vessel prosthesis.

20 Claims, 9 Drawing Sheets

GUIDEWIRE WITH TWO FLEXIBLE END PORTIONS AND METHOD OF ACCESSING A BRANCH VESSEL THEREWITH

FIELD OF THE INVENTION

The invention relates to medical guidewires used to assist in the placement of catheters in the vasculature, and particularly to a guidewire having flexible proximal and distal end portions to assist in the placement of a prosthesis in a branch or side vessel.

BACKGROUND OF THE INVENTION

Medical guidewires are used in numerous catheterization procedures as an aid to placement of a catheter and/or prosthesis at a selected site within a body lumen. The catheter is constructed to perform a particular procedure at that internal site. Among the more common uses of guidewire is in the catheterization of blood vessels for diagnostic or therapeutic purposes. In such a vascular catheterization procedure, the guidewire is inserted, usually percutaneously, into one of the patient's blood vessels and is manipulated and advanced through the branches of the vascular system to the target site. The catheter is then threaded over and advanced along the guidewire, with the guidewire serving to guide the catheter directly to the target site.

Guidewires may be extremely slender, in the order of 0.25 to 0.46 mm (0.010 to 0.018 inches) in diameter, but nevertheless must be capable of transmitting rotation from the guidewire proximal end to the distal end so that a clinician may controllably steer the guidewire through the branches of the patient's arteries and manipulate it to the target site in the intended body lumen. Additionally, the distal region of the guidewire must be sufficiently flexible to pass through sharply curved tortuous coronary anatomy, as well as to provide a sufficiently soft, distal tip that will not injure the artery. In addition, the guidewire must have sufficient column strength so that it can be pushed without buckling.

A guidewire configuration used in angioplasty is illustrated in U.S. Pat. No. 4,545,390 to Leary. Such a wire includes an elongate flexible shaft, typically formed from stainless steel, having a tapered distal region and a helical coil mounted to and about the tapered distal region. The generally tapering distal region of the shaft acts as a core for the coil and results in a guidewire having a distal region of increasing flexibility that is adapted to follow the contours of the vascular anatomy while still being capable of transmitting rotation from the proximal end of the guidewire to the distal end, so that the physician can controllably steer the guidewire through the patient's blood vessels.

Performance characteristics of the guidewire are affected by the construction of the guidewire distal tip. For example, in one type of tip construction, the tapering core wire extends fully through the helical coil to the distal tip of the coil and is attached directly to a smoothly rounded tip weld at the distal tip of the coil. Such a construction, referred to as a core-to-tip construction, typically results in a relatively stiff tip particularly suited for use through tight stenosis. In addition to a high degree of column strength, such a tip also displays excellent torsional characteristics.

In another type of tip construction, the tapered core wire terminates short of the tip weld. In such a construction, a very thin metallic ribbon may be attached between a distal end of the core wire and the smoothly rounded tip weld at the distal tip of the coil. The ribbon serves as a safety element to maintain the connection between the core wire and the distal tip weld in the event of coil breakage. It also serves as a shaping ribbon for receiving and retaining a bend or curve to maintain the guidewire distal segment in a bent configuration, as may be desirable when manipulating and steering the guidewire selectively into vessel side branches. Additionally, by terminating the core wire short of the tip weld, the segment of the helical coil between the distal end of the core wire and the tip weld is very flexible or "floppy." The so-called floppy tip is desirable in situations where the vasculature is highly tortuous and in which the guidewire distal segment must be capable of conforming to and following the tortuous anatomy with minimal trauma to the blood vessel.

Floppy guidewire tips are used during implantation of prostheses within blood vessels or other similar organs of the living body. For example, rather than performing an open surgical procedure to implant a stent-graft that may be traumatic and invasive, stent grafts are preferably deployed through a less invasive intraluminal delivery. Prosthetic vascular stent grafts constructed of biocompatible materials, such as Dacron or expanded, porous polytetrafluoroethylene (PTFE) tubing, have been employed to replace or bypass damaged or occluded natural blood vessels. A lumen of the vasculature is accessed at a convenient and low trauma entry point, and a self-expanding compressed stent graft is routed through the vasculature to the site where the prosthesis is to be deployed. The catheter is then routed though a body lumen until the end of the catheter containing the stent graft is positioned at the intended treatment site, and the stent graft is deployed to radially self-expand so that at least a portion of it contacts and substantially conforms to a portion of the surrounding interior wall of the lumen, e.g., the blood vessel wall or anatomical conduit.

Grafting procedures are known for treating aneurysms. Aneurysms result from weak, thinned blood vessel walls that "balloon" or expand due to aging, disease and/or blood pressure in the vessel. Consequently, aneurysmal vessels have a potential to rupture, causing internal bleeding and potentially life threatening conditions. Grafts are often used to isolate aneurysms or other blood vessel abnormalities from normal blood pressure, reducing pressure on the weakened vessel wall and reducing the chance of vessel rupture. As such, a tubular endovascular graft may be placed within the aneurysmal blood vessel to create an artificial flow conduit through the aneurysm, thereby reducing if not nearly eliminating the exertion of blood pressure on the aneurysm.

While aneurysms can occur in any blood vessel, most occur in the aorta and peripheral arteries. Depending on the region of the aorta involved, the aneurysm may extend into areas having vessel bifurcations or segments of the aorta from which smaller "branch" arteries extend. Various types of aortic aneurysms may be classified on the basis of the region of aneurysmal involvement. For example, thoracic aortic aneurysms include aneurysms present in the ascending thoracic aorta, the aortic arch, and branch arteries that emanate therefrom, such as subclavian arteries, and also include aneurysms present in the descending thoracic aorta and branch arteries that emanate therefrom, such as thoracic intercostal arteries and/or the suprarenal abdominal aorta and branch arteries that emanate therefrom, such as superior mesenteric, celiac and/or intercostal arteries. Lastly, abdominal aortic aneurysms include aneurysms present in the aorta below the diaphragm, e.g., pararenal aorta and the branch arteries that emanate therefrom, such as the renal arteries.

Unfortunately, not all patients diagnosed with aortic aneurysms are presently considered to be candidates for endovascular grafting. This is largely due to the fact that most of the endovascular grafting systems of the prior art are not designed for use in regions of the aorta from which side branches extend. The deployment of endovascular grafts within regions of the aorta from which branch arteries extend presents additional technical challenges because, in those cases, the endovascular graft must be designed, implanted, and maintained in a manner which does not impair the flow of blood into the branch arteries.

To accommodate side branches, a main vessel stent graft having a fenestration or opening in a side wall thereof is often used. The fenestration is positioned to align with or at least be in the vicinity of the ostium of the branch vessel after deployment. In use, the proximal end of the graft having one or more side openings is securely anchored in place, and the fenestrations or openings are configured and deployed to avoid blocking or restricting blood flow into the side branches. Fenestrations alone do not form discrete conduit(s) through which blood is channeled into each side branch artery. As a result, the edges of the graft surrounding the fenestrations are prone to: i) the leakage of blood into the space between the outer surface of the aortic graft and the surrounding aortic wall; or ii) post-implantation migration or movement of the stent graft causing misalignment of the fenestration(s) and the branch artery(ies), which may result in impaired flow into the branch artery(ies).

In some cases, another stent graft, often referred to as a branch prosthesis, may then be deployed through the fenestration into the branch vessel to provide a conduit for blood flow to the branch vessel. The branch prosthesis is preferably sealingly connected to the main graft in situ to prevent undesired leakage.

Delivery of multiple stent grafts in a single procedure may involve multiple guidewires and/or additional procedural steps to manipulate the guidewire(s) and catheter(s) involved in placement thereof. There remains a need in the art for improvements for implantation branch prostheses for improving flow into the corresponding branch vessels. Embodiments hereof relate to a guidewire having floppy tips at both ends thereof to assist in the placement of a branch prosthesis.

SUMMARY

Embodiments of the present invention relate to a method of percutaneously accessing a branch vessel through a deployed prosthesis having at least one fenestration positioned within the vicinity of an ostium of the branch vessel utilizing a guidewire having flexible proximal and distal end portions or tips. The prosthesis is deployed through a first percutaneous access site such that the at least one fenestration is located near the ostium of the branch vessel, wherein a flexible distal end portion of a guidewire is threaded through the at least one fenestration of the prosthesis. The flexible distal end portion is then snared via a second percutaneous access site and pulled in a direction towards the second percutaneous access site until the flexible proximal end of the guidewire is located adjacent to the ostium of the branch vessel. A guide catheter is then advanced over the guidewire until a distal end of the guide catheter is located within the fenestration and at least near the ostium of the branch vessel. The flexible proximal end of the guidewire is then advanced into the branch vessel.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
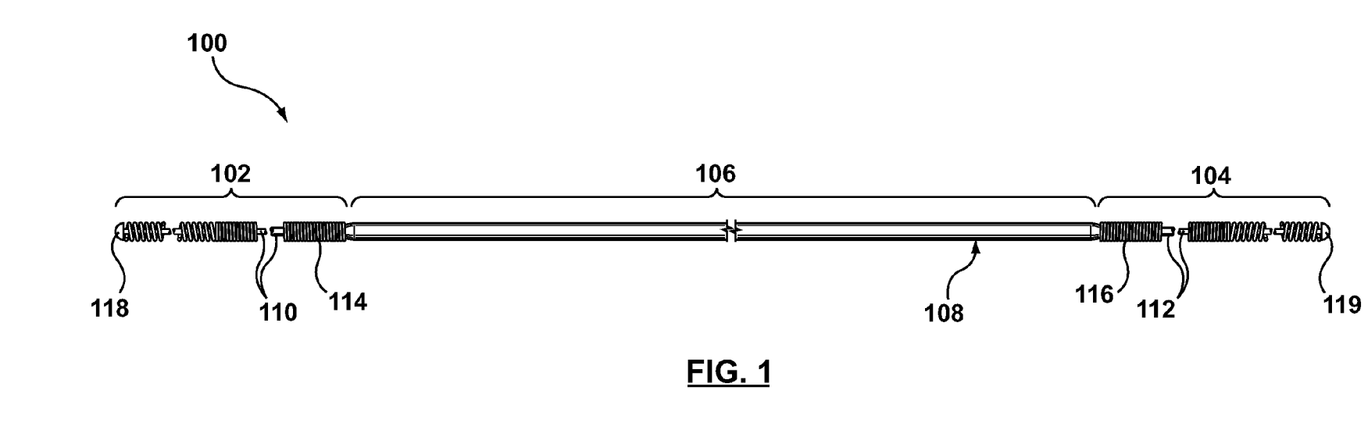
FIG. 1 is a side view of a guidewire having floppy tips at both ends thereof according to an embodiment hereof.

FIG. 1 illustrates a steerable guidewire 100 having a proximal end or tip portion 102, a distal end or tip portion 104, and an intermediate portion or body 106 extending therebetween. Both proximal end portion 102 and distal end portion 104 are each of greater flexibility than elongate body 106. Elongate body 106 includes an elongate flexible shaft 108 such as a solid wire or a tubular component with sufficient column strength to be pushed through a patient's vascular system without kinking and is also flexible enough to avoid damaging the blood vessel or other body lumen through which guidewire 102 is advanced. Shaft 108 may be constructed from any suitable material, including stainless steel and NiTi alloys such as nitinol. A steerable guidewire that may be adapted for use in embodiments hereof is described in U.S. Pat. No. 4,545,390 to Leary, which is incorporated by reference herein in its entirety.

Proximal and distal end portions 102, 104 are both constructed to be very flexible or "floppy" such that each end portion is capable of conforming to and following the contours of highly tortuous vascular anatomy. More particularly, proximal and distal end portions 102, 104 are constructed to have to less stiff than the body 106. Stiffness refers to the resistance of an elastic body to deflection or deformation by an applied force. In one embodiment, body 106 has a stiffness ratio relative to the proximal and distal end portions 102, 104 in the range of 14:1 to 1500:1 as described in the article "The Mechanical Properties of Guidewires. Part I: Stiffness and Torsional Strength" by Jorgen Schroder (2003), herein incorporated by reference in its entirety. Proximal and distal end portions 102, 104 may be of similar construction and stiffness. In another embodiment, proximal and distal end portions 102, 104 may be of different constructions resulting in differing stiffnesses, although each end portion must be sufficiently flexible to access vascular anatomy without damage thereto. Proximal and distal end portions 102, 104 may include any suitable construction in order to achieve the desired amount of flexibility. For example, as shown in FIG. 1, end portions 102, 104 may each include a tapered core wire 110, 112, respectively, and a helical coil 114, 116, respectively, that is attached to and extends about the tapered core wires 110, 112, respectively. In one embodiment, polymer jackets (not shown) formed from polyurethane may be included around helical coils 114, 116, respectively, for providing a smooth and slidable outer surface. Tapered core wires 110, 112 may be integrally formed or mechanically coupled to shaft 108 of body 106. Tapered core wires 110, 112 may include a continuous taper as shown, or may alternatively include a stepped taper. In addition, the ends or tips of tapered core wires 110, 112 may be include a relatively rounded tip 118, 119, respectively, as shown, or may alternatively the ends or tips of tapered core wires 110, 112 may be relatively blunt or pointed. Exemplary suitable constructions for proximal and distal end portions 102, 104 are described in U.S. Pat. No. RE 37,148 to Shank or U.S. Published Patent Application Publication No. 2007/0244413 to Biggins, the disclosures of which are hereby incorporated by reference herein in their entirety, or may include other guidewire tip constructions resulting in a flexibility suitable for accessing vascular anatomy with damage thereto.

Figure 2:
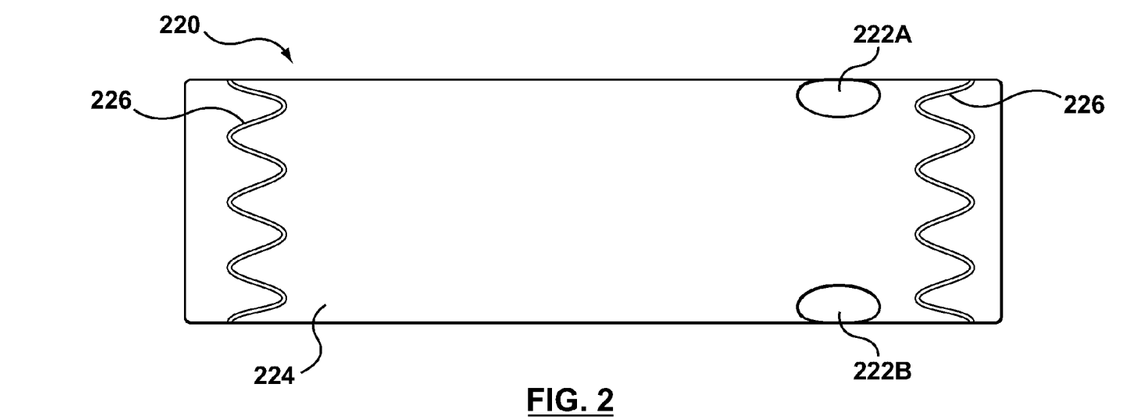
FIG. 2 is a side view of a graft prosthesis for utilization with the guidewire of FIG. 1 according to an embodiment hereof.

Guidewire 100 has particular utility in accessing a branch vessel during an endovascular aneurysm repair. More particularly, turning to FIG. 2, an exemplary graft prosthesis 220 having two side openings or fenestrations 222A, 222B that extend from an inner surface of prosthesis 220 to an outer surface of prosthesis 220 that are used to permit blood flow into two opposing side branch vessels. As depicted in FIG. 2, fenestrations 222A, 222B may be pre-formed on prosthesis 220 prior to insertion of the prosthesis into the patient. When deployed with a main vessel such as the aorta, prosthesis 220 is positioned such that fenestrations 222A, 222B align with, are adjacent to, or are at least in the vicinity of the ostium of opposing branch vessels, such as the renal arteries. Prosthesis 220 includes a synthetic graft material shaped as a tubular body 224. Prosthesis 220 may include one or more annular support members or stents 226 attached thereto for supporting the ends thereof. FIG. 2 illustrates two stents 226 attached to the top and bottom edges of the graft material; however, a greater or lesser number of stents may be used. Stents 226 may have any suitable configuration. Examples of such annular support structures are described, for example, in U.S. Pat. No. 5,713,917 and U.S. Pat. No. 5,824,041, which are incorporated by reference herein in their entirety. When used in an aneurysm exclusion device, the stents have sufficient radial spring force and flexibility to conformingly engage the prosthesis with the body lumen inner wall, to avoid excessive leakage, and prevent pressurization of the aneurysm, i.e., to provide a leak-resistant seal. Although some leakage of blood or other body fluid may occur into the aneurysm isolated by the graft prosthesis, an optimal seal will reduce the chances of aneurysm pressurization and resulting rupture. Stents 226 are preferably a self-expanding spring member that is deployed by release from a restraining mechanism, such as a sheath. For example, stents 226 may be constructed of a superelastic material, such as nitinol.

Figure 3:
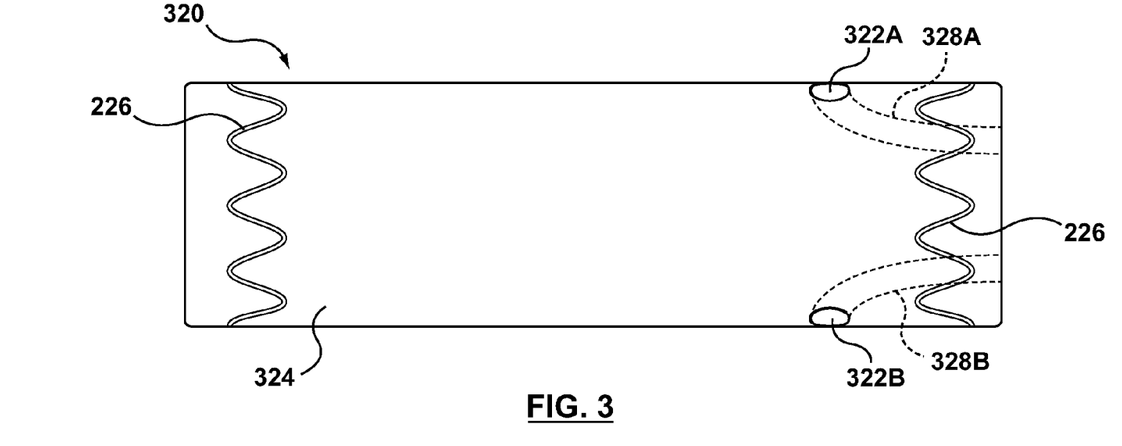
FIG. 3 is a side view of a graft prosthesis for utilization with the guidewire of FIG. 1 according to another embodiment hereof.

FIG. 3 illustrates an alternative configuration of a graft prosthesis 320 that may be deployed with the assistance of guidewire 100. Similar to prosthesis 220 described above, prosthesis 320 includes a synthetic graft material shaped as a tubular body 324 and may include one or more stents 326 attached thereto for supporting the ends thereof. In this embodiment however, prosthesis 320 includes two opposing internal conduits or passageways 328A, 328B formed within a sidewall of prosthesis 320 that terminate in fenestrations 322A, 322B, respectively. Internal conduits 328A, 328B extend from an inner surface of prosthesis 220 to an outer surface of prosthesis 320 and are used to direct blood flow into two opposing side branch vessels.

It will be understood by those of ordinary skill in the art that guidewire 100 may be used to deliver and deploy a graft prosthesis of any suitable configuration. For example, a graft prosthesis may include one or more external conduits or couplings that extend from an outside surface of the graft and into the ostium(s) of one or more branch vessel(s). In addition, multiple modular graft prostheses may be deployed at a target site such as a main trunk having a cylindrical configuration for deployment in the aorta and a bifurcated prosthesis having a "Y" or forked configuration for deployment in the aorta and the femoral artery branches. Other exemplary graft prostheses that may be deployed with the assistance of guidewire 100 are shown and described in the articles "Endovascular Repair of Thoracoabdominal Aneurysms" by Greenberg et al. (2008) and "Branched devices for thoracoabdominal aneurysm repair: Early experience" by Ferreira et al. (2008), each of which are herein incorporated by reference in their entirety. Further, it is not required that the graft prosthesis be self-expandable. Rather, the graft prosthesis may be partially or fully balloon-expandable.

Figure 4:
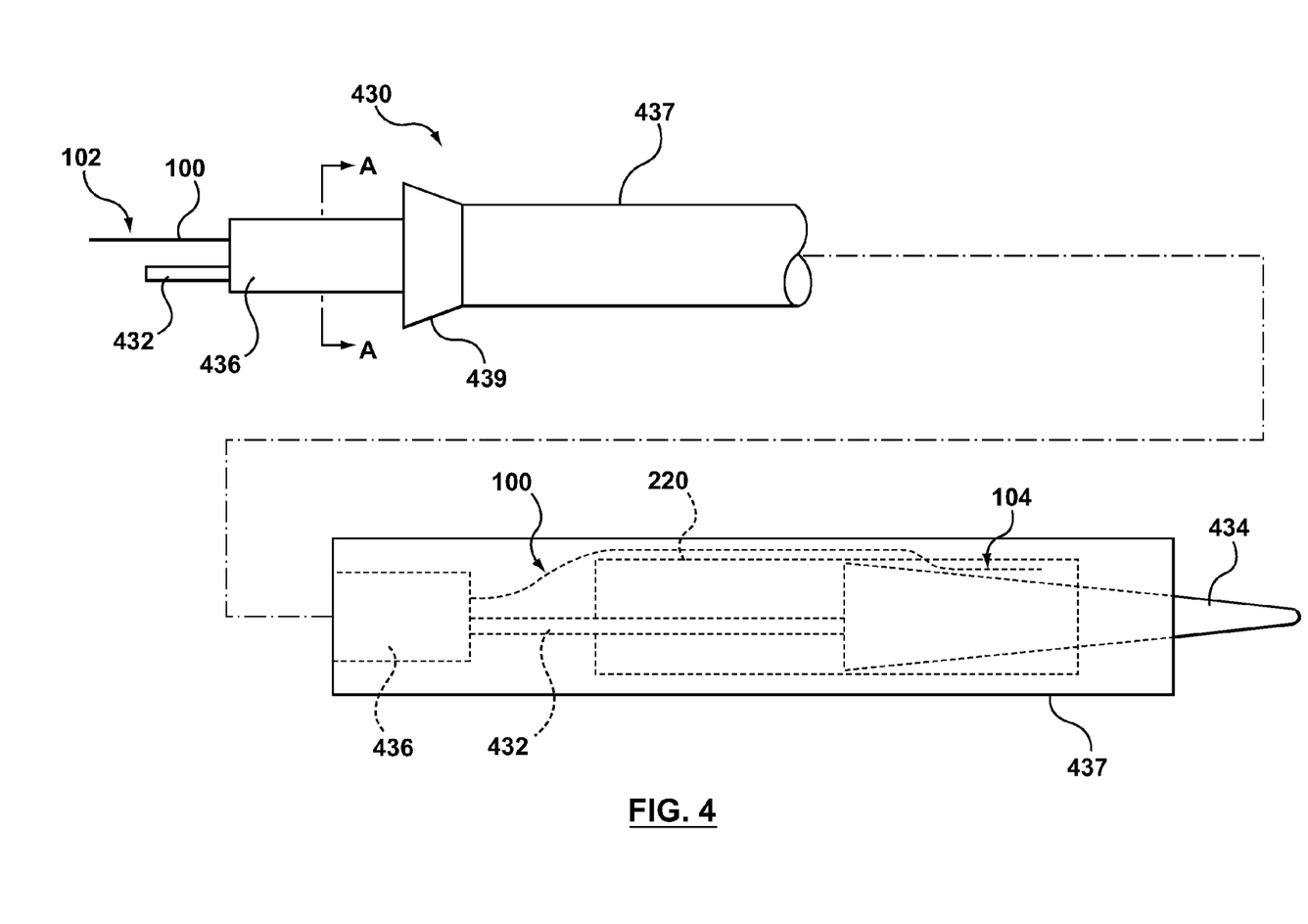
FIG. 4 is a side view of a delivery system for the graft prosthesis of FIG. 2 according to an embodiment hereof.
Figure 4A:
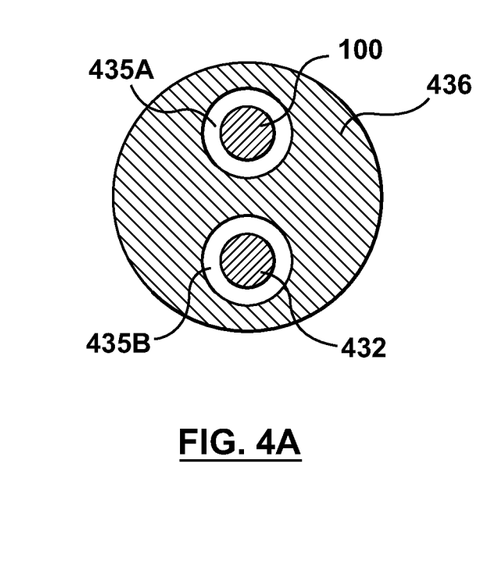
FIG. 4A is a cross-sectional view taken along line A-A of FIG. 4.

Turning now to FIGS. 4 and 4A, a delivery system 430 for delivering and deploying a self-expanding prosthesis 220 is shown. Delivery system 430 includes a retractable sheath 437, a multi-lumen extruded outer shaft 436, and an inner shaft 432. Retractable sheath 437 is an elongated tubular component that is provided to cover prosthesis 220 during delivery and is selectively movable in an axial direction (i.e., along and relative to outer shaft 436) via a handle 439 to selectively expand prosthesis 220. Prosthesis 220 is mounted on a distal portion of inner shaft 432, and retractable sheath 437 in a non-retracted or delivery position contains prosthesis 220 in a constrained diameter configuration as shown in FIG. 4. Inner shaft 432 extends through a lumen 435B of outer shaft 436 to a distal tip 434 of system 100. Distal tip 434 is coupled to a distal end of inner shaft 432, and may be tapered and flexible to provide trackability in tight and tortuous vessels. As shown, inner shaft 432 may be a solid rod that is tracked to the target site with the assistance of tapered distal tip 434. In another embodiment (not shown), inner shaft 432 and distal tip 434 may define a guidewire lumen (not shown) for receiving a guidewire (not shown) therethrough. When the guidewire lumen is present, inner shaft 432 and distal tip 434 may be advanced over an indwelling guidewire to track the delivery system to the target site.

In one embodiment, guidewire 100 is preloaded through delivery system 430 and prosthesis 220 prior to introduction into the vasculature. More particularly, as shown in FIGS. 4 and 4A, guidewire 100 extends through a lumen 435A of outer shaft 436, exits a distal end of outer shaft 436, and runs along an outer surface of prosthesis 220. Distal end 104 of guidewire 100 is threaded through fenestration 222A such that distal end 104 runs along an inside surface of prosthesis 220 and is housed within prosthesis 220 during delivery.

Figure 4B:
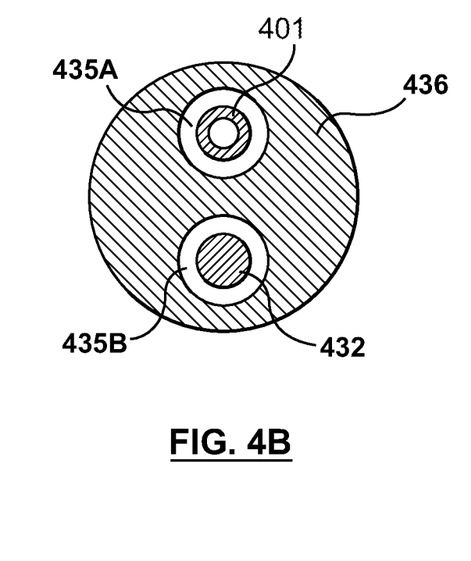
FIG. 4B is a cross-sectional view taken along line A-A of FIG. 4 according to another embodiment hereof.

In another embodiment depicted in the cross-sectional view of FIG. 4B, a retractable tube or tubular component 401 may be preloaded through delivery system 430 and prosthesis 220 prior to introduction into the vasculature. More particularly, retractable elongated tubular component 401 has an inner diameter sized to slidingly receive guidewire 100. Similar to the preloading configuration of guidewire 100 described above, tubular component 401 extends through a lumen 435A of outer shaft 436, exits a distal end of outer shaft 436, runs along an outer surface of prosthesis 220, 320 and is threaded through fenestration 222A, 322A such that a distal end of tubular component 401 is housed within prosthesis 220, 330 during delivery. By preloading tubular component 401 rather than guidewire 100, a physician may select the particular dimensions or properties of guidewire 100 to be used in a procedure. For example, the outer diameter or flexibility of proximal and/or distal tips 102, 104 may vary and be configured for particular applications and accordingly a physician may select an appropriate guidewire size or flexibility to suit the target body lumen. Guidewire 100 may be slidingly delivered through the lumen of tubular component 401 and be effectively positioned in the same preloaded configuration as described above with respect to FIGS. 4 and 4A. Once distal end 104 of guidewire 100 is threaded through fenestration 222A, 322A and housed within prosthesis 220, 320, tubular component 401 may be retracted and removed from the patient. Guidewire 100 may be positioned through tubular component 401 before or after delivery system 430 is introduced into the vasculature.

Prosthesis 220 may be mounted on the distal portion of inner shaft 432 by any suitable configuration known in the art. For example, prosthesis may be maintained in a radially compressed or delivery configuration simply by outer sheath 437. Alternatively, attachment bands extending between the graft and the inner shaft may be used for acting as a means for retaining the graft in place during delivery. The attachment bands eventually release the graft by self-expansion. Other means may be used for retaining the graft in place within delivery system 430 during delivery, or for controlled release of prosthesis 220 when outer sheath 43 is retracted. For example, the graft may be held in frictional engagement with the delivery system by the inclusion of slots, ridges, pockets, or other prosthesis retaining features (not shown) formed into the exterior surface of the inner shaft to further ensure secure mounting of the graft as it is tracked transluminally to the target site. In addition, a cap may be coupled to the distal end of the inner shaft to retain the graft in a radially compressed configuration. An actuator at the proximal portion of the system may precisely control the release of the graft from the cap and from the radially compressed configuration. An exemplary stent graft delivery system that may be adapted for use herein is described in U.S. Pat. No. 7,264,632 to Wright et al., which is hereby incorporated by reference in its entirety, or other such similar delivery systems well known in the art.

Other types of delivery systems are also amendable to the present invention, such as, without limitation thereto, a delivery system for a balloon-expandable graft prosthesis. With respect to a delivery system balloon-expandable prosthesis, a pre-loaded guidewire 100 or tubular component 401 would extend through a lumen of the delivery system, run along an outer surface of the balloon-expandable prosthesis, and be threaded through a fenestration in the prosthesis such that the distal end of the guidewire 100 or tubular component 401 runs between an inside surface of the prosthesis and the balloon of the delivery system during delivery.

FIGS. 5-9 are illustrations of utilizing guidewire 100 for placement of graft prosthesis 220 within a side or branch vessel according to an embodiment hereof. More particularly, turning to FIG. 5, prosthesis 220 having two side openings or fenestrations 222A, 222B is shown deployed within a main vessel MV, i.e., subsequent to retraction of retractable sheath 437 (not shown in FIGS. 5-9). Although described herein with respect to prosthesis 220, the method described with respect to FIGS. 5-9 may also be used with prosthesis 330 or other prostheses configurations having at least one side opening, fenestration, and/or conduit for providing blood flow to a branch vessel. Further, although described herein with respect to a preloaded guidewire 100, the method described with respect to FIGS. 5-9 may also be used with a pre-loaded tube as described with respect to FIG. 4B.

Figure 5:
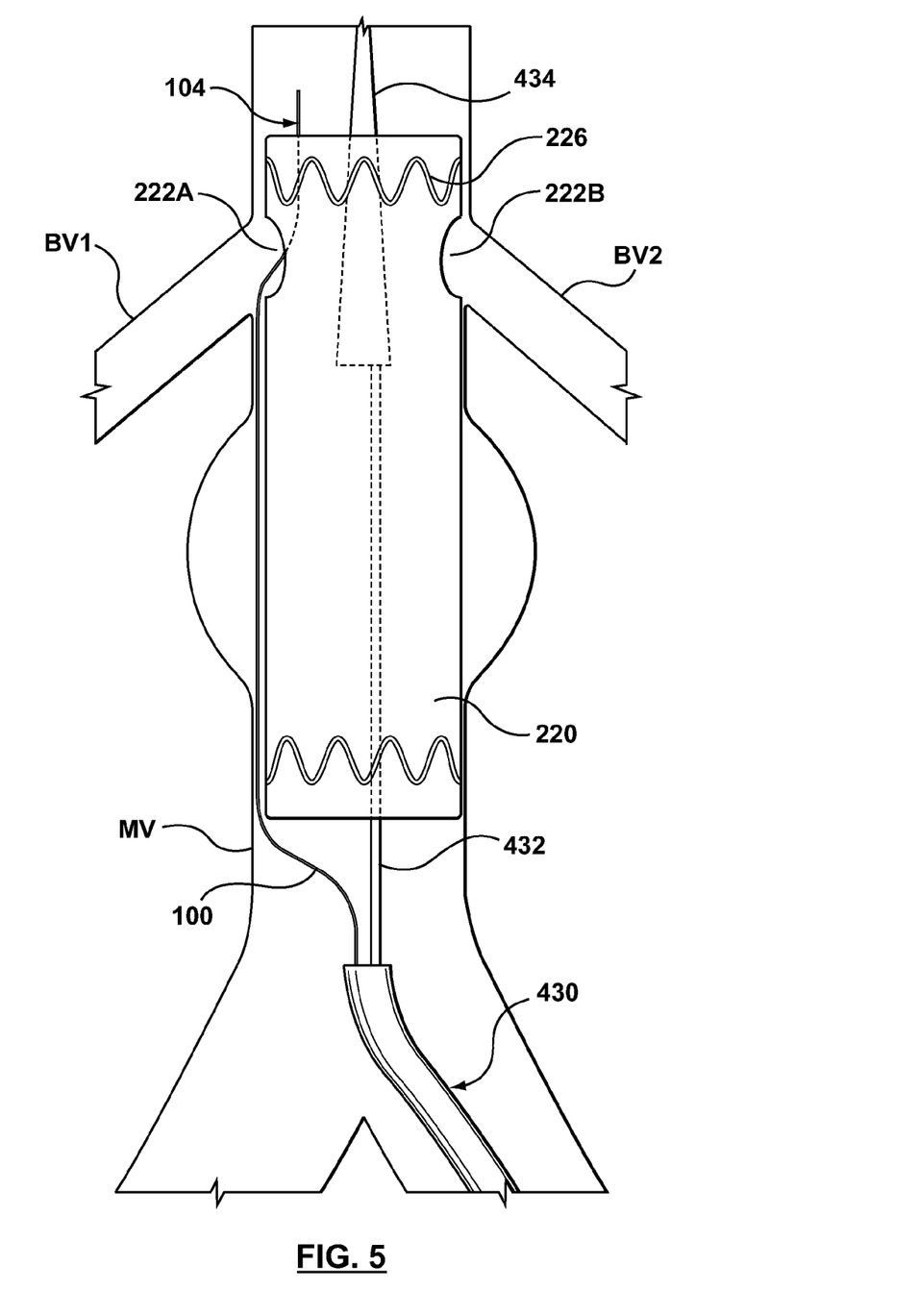
FIGS. 5-9 are illustrations of utilizing the guidewire of FIG. 1 for placement of the graft prosthesis of FIG. 2 within a side or branch vessel according to an embodiment hereof.

In FIG. 5, main vessel MV is the aorta. The target branch vessels BV1 and BV2 depend on the region of the aorta involved. For example, the branch arteries that emanate from the descending thoracic aorta include the thoracic intercostal arteries and the branch arteries that emanate from the suprarenal abdominal aorta include the superior mesenteric, celiac and/or intercostal arteries. The branch arteries that emanate from the pararenal aorta include the renal arteries. Delivery system 430, and thus prosthesis 220 and preloaded guidewire 100, is introduced into the vasculature through a first percutaneous access site such as a branch of a femoral artery, is delivered to the target location within main vessel MV, and is deployed into apposition with the vessel wall at the target location as shown in FIG. 5. Surgical methods and apparatus for delivering prosthesis 220 intravascularly are generally known in the art and may be used to place the delivery system within the vasculature and deliver prosthesis 220 to the deployment site. For example, prosthesis 220 may be guided to the deployment site using fluoroscopic imaging such that fenestrations 220A, 220B may be properly aligned with the ostiums of branch vessels BV1, BV2, respectively.

Figure 6:
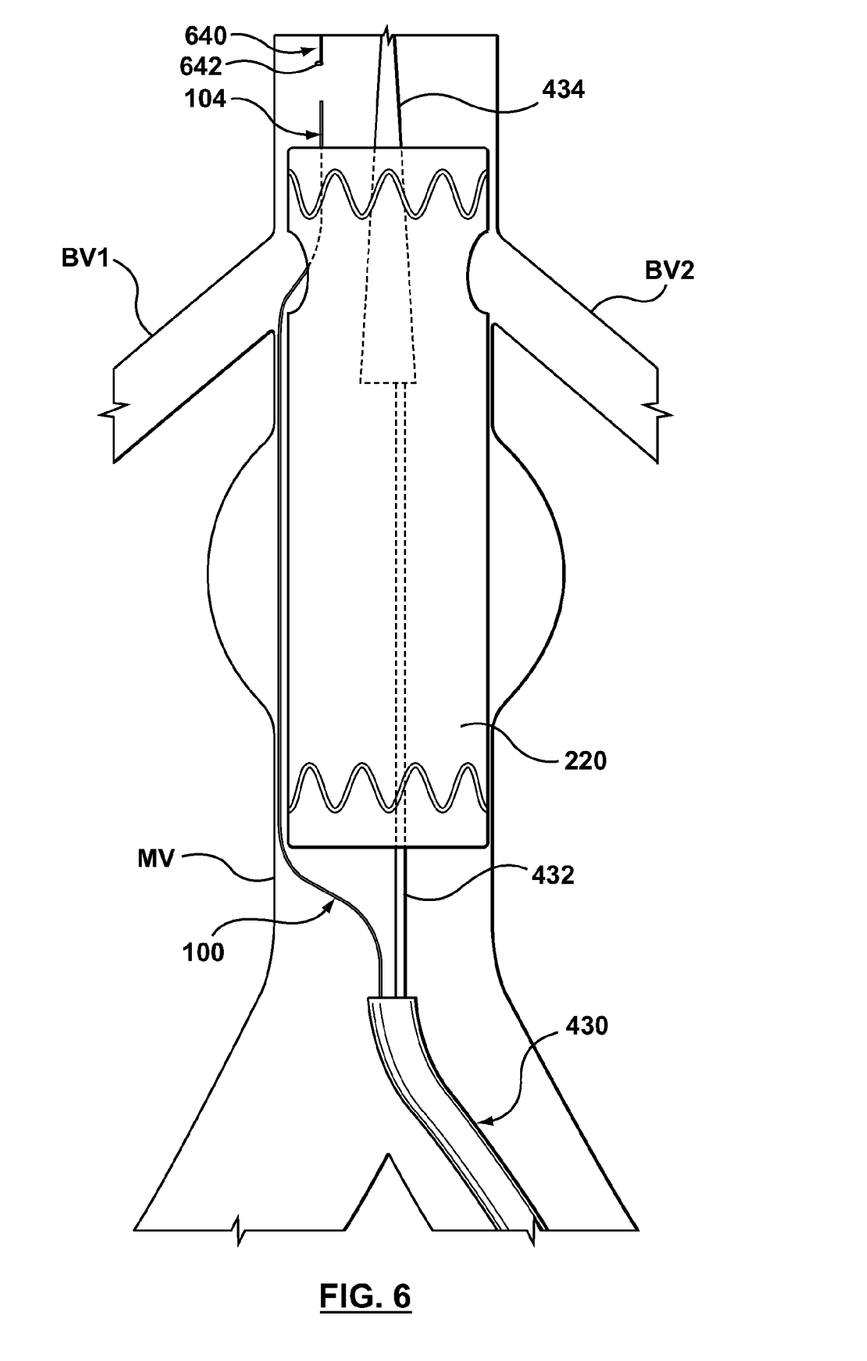
Figure 7:
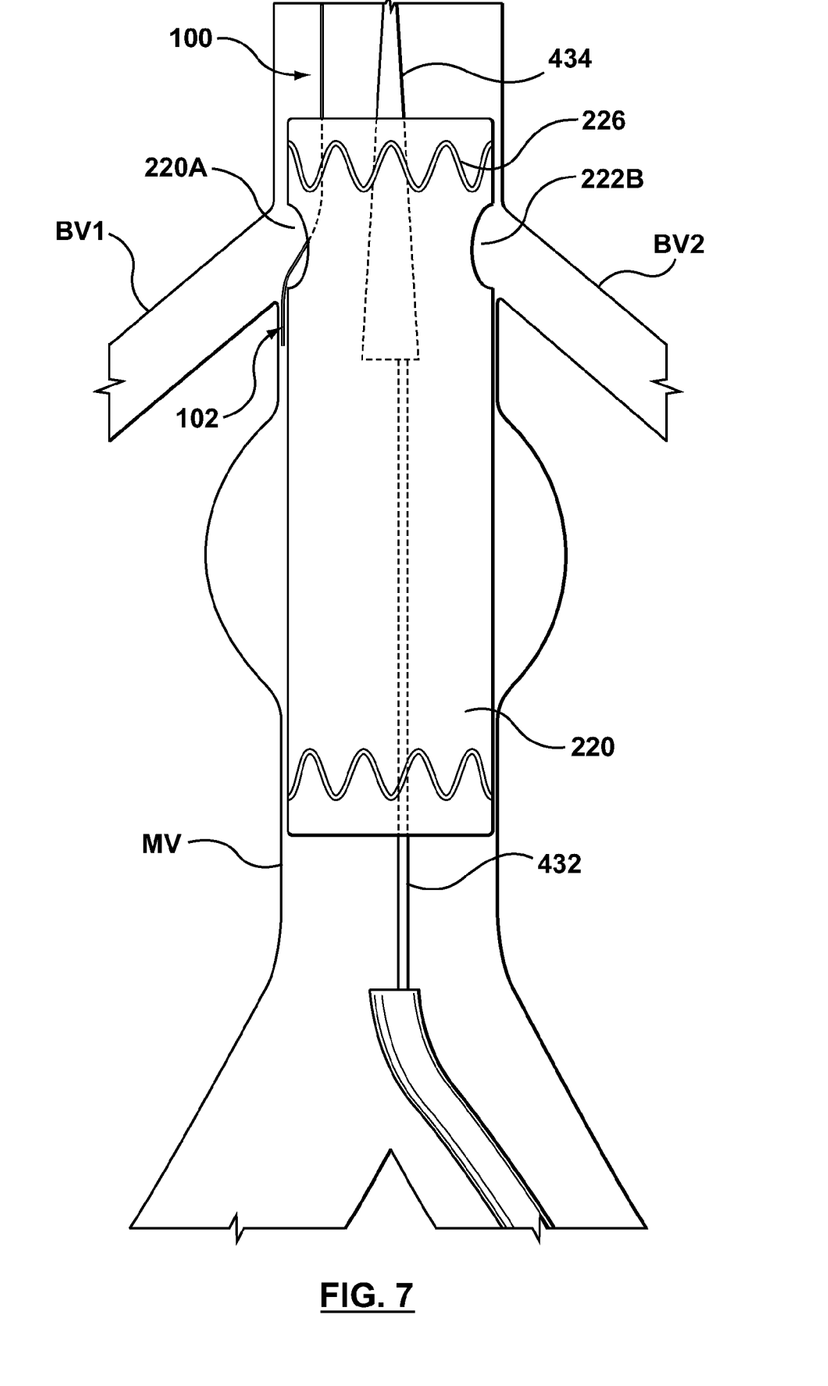

Referring now to FIG. 6, a snare 640 is delivered to the deployed prosthesis 220 via a second percutaneous access site. In one embodiment hereof, the second percutaneous access site is located on the opposite side of graft 220 as the first percutaneous access site. For example and not by way of limitation, the second percutaneous access site may be one of the brachial arteries, which accesses the aorta through one of the subclavian arteries, or the second percutaneous access site may be the one of the subclavian arteries. Snare 640 may be any suitable device having a distal end capable of capturing or catching the distal end of the guidewire, including for example, and not by way of limitation, snares commercially available from Abbott Vascular of Abbott Park, Ill., Vascular Solutions, Inc. of Minneapolis, Minn., Cook Medical of Bloomington, Ind., or ev3, Inc. of Plymouth, Minn. For example, a looped distal end 642 of snare 640 captures or catches distal end 104 of guidewire 100, and snare 640 pulls guidewire 100 until distal end 104 is pulled to a position outside of the patient. Due to the "floppy" or flexible nature of distal end 104, guidewire 100 may be safely proximally pulled through the vasculature without risk of inadvertently piercing through a vessel wall. Distal end 104 is pulled or proximally retracted in a direction towards the second percutaneous access site until proximal end 102 of guidewire 100 is near or adjacent to the ostium of branch vessel BV1 as shown in FIG. 7. Guidewire 100 is still threaded through fenestration 222A of prosthesis 220.

Figure 8:
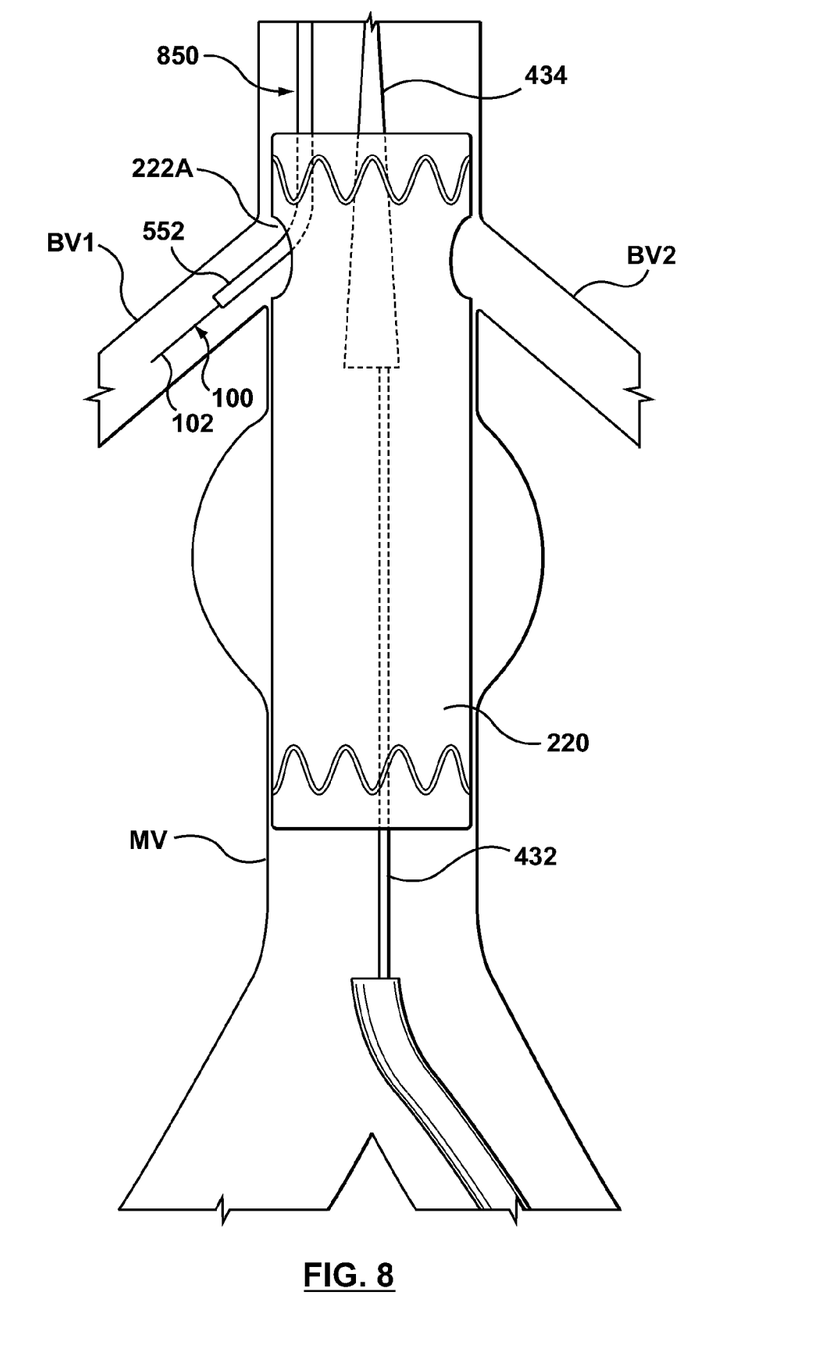

A guide catheter 850 is then tracked over guidewire 100 via the second percutaneous access site until a distal end 852 of guide catheter 850 cannulates or extends into branch vessel BV1 as shown in FIG. 8. Although it is not required that distal end 852 of guide catheter 850 extend into the branch vessel, the distal end of the guide catheter should be positioned to extend at least within the fenestration and near the ostium of the branch vessel. In one embodiment hereof, the second percutaneous access site is advantageously located such that the target branch vessel BV1 extends at an obtuse angle from the main vessel relative to the direction of the second percutaneous access site in order to allow for easy access to branch vessel BV1 from the direction of the second percutaneous access site. More particularly, because branch vessel BV1 extends at an acute angle from the main vessel relative to the direction of the first percutaneous access site in FIGS. 5-9, it may be difficult to gain access to branch vessel BV1 from the first percutaneous access site. This can be a common problem for the abdominal aorta where many of the branch vessels extend towards the lower extremities of the body and a preferred first percutaneous access site is in the region of the upper thigh, i.e, the femoral artery. Locating and accessing the ostium of the branch vessel is often easier from a location such that the branch vessel extends at an obtuse angle from main vessel, in this case, in a direction from the aortic arch, rather than from a location where the branch vessel extends at an acute angle from the main vessel. Guide catheter 850 may be any suitable sheath or device suitable for cannulating a branch vessel, including but not limited to U.S. Pat. No. 5,492,530 to Fischell et al., herein incorporated by reference in its entirety. In one embodiment, guide catheter 850 includes a curved distal end for cannulating branch vessel BV1. As known by those of ordinary skill in the art, a guide catheter having a curved distal end straightens with a guidewire inserted therethrough. Thus, it may be necessary to retract guidewire 100 to allow the curved distal end of guide catheter 850 to resume its curved shape for cannulating branch vessel BV1. After guide catheter 850 extends into branch vessel BV1, proximal end 102 of guidewire 100 may then be advanced into branch vessel BV1. Since proximal end 102 is floppy and flexible, it accesses and protrudes into branch vessel BV1 without causing damage thereto. If proximal end 102 of guidewire 100 was not sufficiently flexible to protrude into branch vessel BV1, guidewire 100 would need to be completely retracted and removed from, flipped around, and re-inserted into the second percutaneous access site such that floppy and flexible distal end 104 would protrude into the branch vessel BV1. However, by constructing guidewire 100 with two floppy ends, complete retraction and removal of guidewire 100 is not required.

Figure 9:
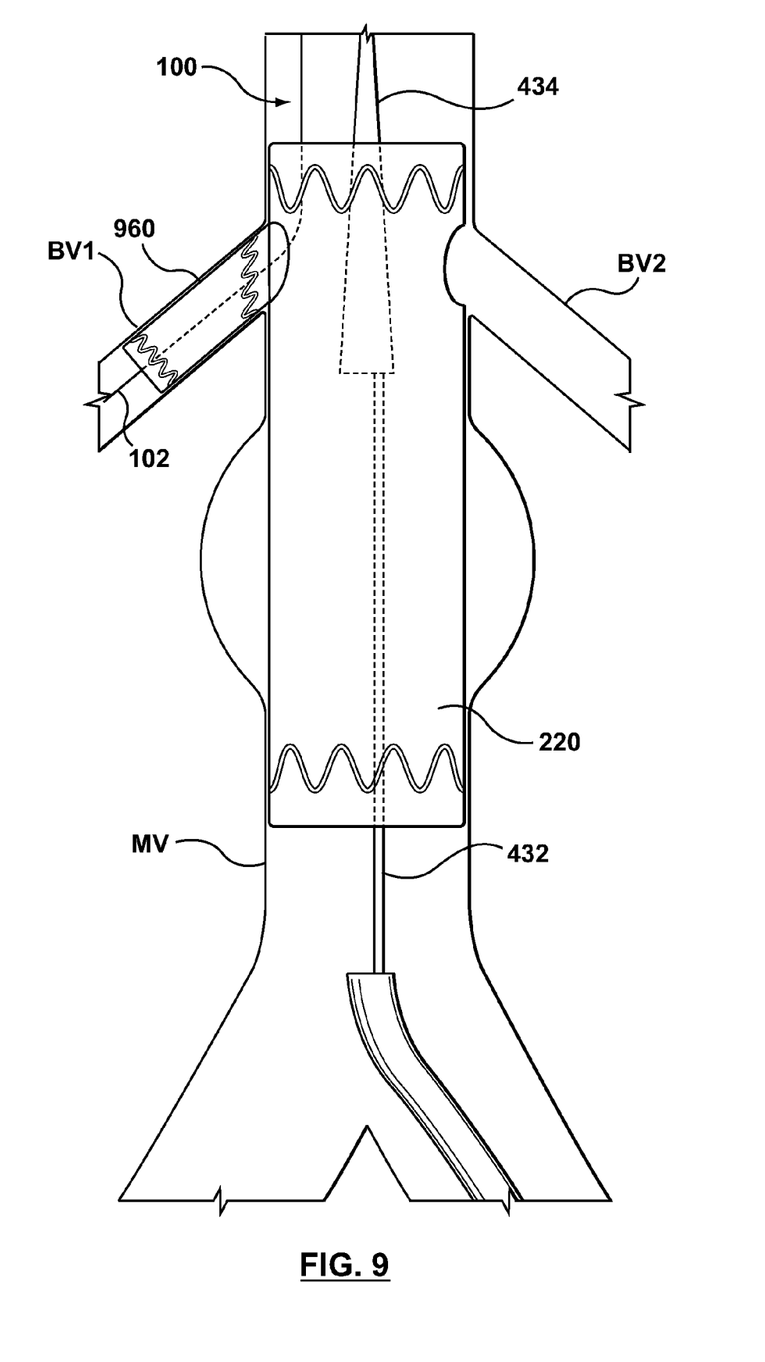

With flexible proximal end 102 positioned within the branch vessel BV1, a branch prosthesis or conduit 960 may be subsequently delivered over indwelling guidewire 100 to isolate the portion of the aneurysm in branch vessel BV1 as shown in FIG. 9. Branch prosthesis 960 may be a self-expanding or balloon-expandable stent-graft device known in the art, and may be delivered by a delivery catheter (not shown) such as but not limited to delivery system 430 described above in relation to prosthesis 220.

Although described herein as using guidewire 100 for accessing branch vessel BV1, it will be understood by those of ordinary skill in the art that guidewire 100 may be used for accessing branch vessel BV2. Further, multiple guidewires having proximal and distal flexible end portions may be preloaded into fenestrations of the main vessel prosthesis and used for simultaneously accessing multiple branch vessels aligned with the fenestrations.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of percutaneously accessing a branch vessel through an at least partially deployed prosthesis having at least one fenestration positioned in the vicinity of an ostium of the branch vessel, the method comprising:
   at least partially deploying the prosthesis through a first percutaneous access site such that the at least one fenestration is positioned in the vicinity of the ostium of the branch vessel, wherein a flexible distal end portion of a guidewire is disposed at least partially within a lumen of the prosthesis;
   snaring the flexible distal end portion of the guidewire via a second percutaneous access site;
   pulling the flexible distal end portion of the guidewire in a direction towards the second percutaneous access site until a flexible proximal end of the guidewire is located adjacent to the ostium of the branch vessel;
   advancing a guide catheter over the guidewire until a distal end of the guide catheter is located within the fenestration and at least near the ostium of the branch vessel; and
   advancing the flexible proximal end of the guidewire into the branch vessel.

2. The method of claim 1, wherein both the flexible distal end portion and the flexible proximal end portion are of greater flexibility than an elongate body of the guidewire.

3. The method of claim 2, wherein the flexible proximal and distal end portions are of the same construction and stiffness.

4. The method of claim 2, wherein the flexible proximal and distal end portions are of differing constructions and stiffnesses.

5. The method of claim 2, wherein the flexible proximal and distal end portions each include a tapered core wire and a helical coil that is attached to and extends about the tapered core wires.

6. The method of claim 1, wherein the branch artery emanates from the aorta.

7. The method of claim 1, wherein the flexible distal end portion of the guidewire is threaded through the at least one fenestration of the prosthesis such that the distal end of the guidewire extends from an outer surface of the prosthesis, through the at least one fenestration to the lumen of the prosthesis.

8. The method of claim 7, wherein the guidewire is preloaded in the location with at least a portion of the distal end in the lumen of the prosthesis.

9. The method of claim 1, wherein the first percutaneous access site is located in a direction of a first end of the prosthesis and the second percutaneous access site is located in a direction of a second end the prosthesis opposite the first end.

10. The method of claim 9, wherein the first percutaneous access site is through a femoral artery and the second percutaneous access site is through a brachial artery or a subclavian artery.

11. The method of claim 1, wherein a branch prosthesis is delivered into the branch vessel over the guidewire after the flexible proximal end of the guidewire is advanced into the branch vessel.

12. The method of claim 1, wherein a tube is preloaded in the prosthesis such that a distal end of the tube extends from an outer surface of the prosthesis, through the at least one fenestration, and into the lumen of the prosthesis, and wherein the step of at least partially deploying the prosthesis further comprises the steps of:
   advancing the guidewire through the tube to position the flexible distal end portion of the guidewire at least partially within the lumen of the prosthesis; and withdrawing the tube proximally through the first percutaneous access site, and leaving the flexible distal end portion of the guidewire disposed at least partially within the lumen of the prosthesis.

13. A method of percutaneously accessing a branch vessel through an at least partially deployed prosthesis having at least one fenestration positioned in the vicinity of an ostium of the branch vessel, the method comprising:
   preloading a guidewire through the at least one fenestration of the prosthesis such that a flexible distal end portion of the guidewire is threaded through the at least one fenestration from an outer surface of the prosthesis and into a lumen of the prosthesis;
   percutaneously introducing the prosthesis and the preloaded guidewire into the vasculature via a first access site;
   at least partially deploying the prosthesis such that the at least one fenestration is positioned in the vicinity of the ostium of the branch vessel;
   snaring the flexible distal end portion of the guidewire via a second percutaneous access site;
   pulling the flexible distal end portion of the guidewire in a direction towards the second percutaneous access site until a flexible proximal end of the guidewire is located adjacent to the ostium of the branch vessel;
   advancing a guide catheter over the guidewire until a distal end of the guide catheter is located within the fenestration and at least near the ostium of the branch vessel; and
   advancing the flexible proximal end of the guidewire into the branch vessel.

14. The method of claim 13, wherein both the flexible distal end portion and the flexible proximal end portion are of greater flexibility than an elongate body of the guidewire.

15. The method of claim 13, wherein the first percutaneous access site is located in a direction of a first end of the prosthesis and the second percutaneous access site is located in a direction of a second end the prosthesis opposite the first end.

16. The method of claim 15, wherein the first percutaneous access site is through a femoral artery and the second percutaneous access site is through a brachial artery or a subclavian artery.

17. A method of percutaneously accessing a branch vessel through an at least partially deployed prosthesis having at least one fenestration is positioned in the vicinity of an ostium of the branch vessel, the method comprising the steps of:
   preloading a tube through the at least one fenestration of the prosthesis such that a distal end portion of the tube is threaded through the at least one fenestration from an outer surface of the prosthesis and into a lumen of the prosthesis;
   percutaneously introducing the prosthesis and the preloaded tube into the vasculature via a first access site;
   at least partially deploying the prosthesis such that the at least one fenestration is positioned in the vicinity of the ostium of the branch vessel;
   advancing a guidewire through the tube to position a flexible distal end portion of the guidewire at least partially within the lumen of the prosthesis;
   withdrawing the tube proximally through the first percutaneous access site;
   snaring the flexible distal end portion of the guidewire via a second percutaneous access site;
   pulling the flexible distal end portion of the guidewire in a direction towards the second percutaneous access site until a flexible proximal end of the guidewire is located adjacent to the ostium of the branch vessel;
   advancing a guide catheter over the guidewire until a distal end of the guide catheter is located within the fenestration and at least near the ostium of the branch vessel; and
   advancing the flexible proximal end of the guidewire into the branch vessel.

18. The method of claim 17, wherein both the flexible distal end portion and the flexible proximal end portion are of greater flexibility than an elongate body of the guidewire.

19. The method of claim 17, wherein the first percutaneous access site is located in a direction of a first end of the prosthesis and the second percutaneous access site is located in a direction of a second end the prosthesis opposite the first end.

20. The method of claim 19, wherein the first percutaneous access site is through a femoral artery and the second percutaneous access site is through a brachial artery or a subclavian artery.

\* \* \* \* \*